(12) United States Patent
Plumb

(10) Patent No.: US 10,413,528 B2
(45) Date of Patent: Sep. 17, 2019

(54) METHODS TO INHIBIT INFECTION DURING WOUND HEALING WITH TOPICAL COMPOSITIONS INCLUDING AMINO ACIDS

(71) Applicant: John H. Plumb, Anderson, IN (US)

(72) Inventor: John H. Plumb, Anderson, IN (US)

( * ) Notice: Subject to any disclaimer, the term of this patent is extended or adjusted under 35 U.S.C. 154(b) by 273 days.

(21) Appl. No.: 14/518,449

(22) Filed: Oct. 20, 2014

(65) Prior Publication Data

US 2016/0106715 A1    Apr. 21, 2016

(51) Int. Cl.
| | |
|---|---|
| *A61K 31/4172* | (2006.01) |
| *A61K 31/198* | (2006.01) |
| *A61K 31/405* | (2006.01) |
| *A61K 31/401* | (2006.01) |
| *A61K 31/716* | (2006.01) |
| *A61K 31/202* | (2006.01) |
| *A61K 31/07* | (2006.01) |
| *A61K 31/593* | (2006.01) |
| *A61K 31/355* | (2006.01) |
| *A61K 31/195* | (2006.01) |
| *A61K 33/30* | (2006.01) |

(52) U.S. Cl.
CPC .......... *A61K 31/4172* (2013.01); *A61K 31/07* (2013.01); *A61K 31/195* (2013.01); *A61K 31/198* (2013.01); *A61K 31/202* (2013.01); *A61K 31/355* (2013.01); *A61K 31/401* (2013.01); *A61K 31/405* (2013.01); *A61K 31/593* (2013.01); *A61K 31/716* (2013.01); *A61K 33/30* (2013.01)

(58) Field of Classification Search
CPC ................................................ A61K 31/4172
USPC ........................................................ 424/462
See application file for complete search history.

(56) References Cited

U.S. PATENT DOCUMENTS

| | | | |
|---|---|---|---|
| 3,697,287 A | 10/1972 | Winitz | |
| 3,698,912 A | 10/1972 | Winitz | |
| 3,701,666 A | 10/1972 | Winitz | |
| 4,201,235 A | 5/1980 | Ciavatta | |
| 4,497,800 A | 2/1985 | Larson et al. | |
| 4,778,679 A | 10/1988 | Silvetti | |
| 4,839,159 A * | 6/1989 | Winter ..................... | A61K 8/44 424/59 |
| 4,889,844 A | 12/1989 | Silvetti, Sr. et al. | |
| 5,378,461 A | 1/1995 | Neigut | |
| 5,425,954 A | 6/1995 | Thompson et al. | |
| 5,719,134 A * | 2/1998 | Schmidl .................. | A23L 33/40 514/168 |
| 5,972,999 A | 10/1999 | Murad | |
| 6,046,178 A | 4/2000 | Silvetti, Sr. | |
| 6,291,519 B1 * | 9/2001 | Kis ....................... | A61K 9/0048 514/458 |
| 6,432,422 B1 | 8/2002 | Yasukawa et al. | |
| 7,384,916 B2 | 6/2008 | Patt | |
| 8,530,426 B2 | 9/2013 | Lintner et al. | |
| 8,613,961 B1 | 12/2013 | Filippova et al. | |
| 8,642,655 B2 | 2/2014 | Johnson | |
| 2003/0091601 A1 | 5/2003 | Barbul | |
| 2005/0106194 A1 | 5/2005 | Schiltz | |
| 2006/0211754 A1 | 9/2006 | Yu et al. | |
| 2009/0142389 A1 * | 6/2009 | Yamashita ........... | A61K 8/0208 424/443 |
| 2011/0098229 A1 | 4/2011 | Paul | |
| 2011/0293755 A1 * | 12/2011 | Sigurjonsson ......... | A61K 31/05 424/734 |
| 2012/0020932 A1 * | 1/2012 | Yao ...................... | A61K 9/0024 424/93.7 |
| 2012/0282348 A1 * | 11/2012 | Yates ................... | A61K 9/0014 424/619 |
| 2013/0237505 A1 | 9/2013 | Purcell | |

FOREIGN PATENT DOCUMENTS

| | | | |
|---|---|---|---|
| EP | 0047647 | * | 3/1982 |
| EP | 0221728 | * | 7/1992 |
| WO | 2011103449 A3 | | 8/2011 |

OTHER PUBLICATIONS

Erickson (Quality in Frozen Food, Springer Science & Business Media, Dec. 6, 2012, p. 220).*
Houghton (Am J Clin Nutr 2006;84:694-7).*
Viljanto et al., "Local Hyperalimentation of Open Wounds", British Journal of Surgery Society Ltd., vol. 63: 427-430, 1976, DOI: 10.1002/bjs.1800630603, (Abstract).
Otten et al., "Dietary DRI Reference Intakes; The Essential Guide to Nutrient Requirements", Institute of Medicine of The National Academies, http://www.nal.usda.gov/fnic/DRI/Essential_Guide/DRIEssentialGuideNutReq.pdf, Aug. 26, 2014, pp. 459-465.
Silvetti et al., "An Explanation of the Antibacterial Characteristics of Maltodextrin NF", jmvprod.weebly.com/uploads/1/7/0/3/17038090/caracteristicas_antibacterianas.pdf, Mar. 23, 2014.
Cassino et al., "Effectiveness of Topical Application of Amino Acids to Chronic Wounds: A Prospective Observational Study", Journal of Wound Care, vol. 19, No. 1, Jan. 2010, pp. 29-34.
Maggio et al., "A New Protocol for the Treatment of the Chronic Venous Ulcers of the Lower Limb", Clinical and Experimental Medicine, vol. 12, No. 1, Mar. 2012, pp. 55-60.

(Continued)

*Primary Examiner* — Devang K Thakor
(74) *Attorney, Agent, or Firm* — Gibb & Riley, LLC

(57) ABSTRACT

A method that inhibits infection during wound healing by topical application of a single composition, which contacts a wound for a period of time to initiate wound healing. The single composition may include a mixture of all or some of the amino acids including: histidine monohydrochloride monohydrate; isoleucine; leucine; lysine acetate; methionine; phenylalanine; threonine; tryptophan; valine; alanine; arginine acetate; aspartic acid; glutamine; glycine; proline; serine; and tyrosine, which may provide aqueous mixtures of a range of osmolarities or a powdered mixture of amino acids. The single composition may also include any of a carbohydrate, a mixture of fatty acids, vitamins, and mineral nutrients, and another mixture of amino acid derivatives and preservatives. The number of moles of the carbohydrate is less than and proportional to a sum of the number of moles of any mixture of amino acids in the single composition.

3 Claims, No Drawings

(56) References Cited

OTHER PUBLICATIONS

Abbruzzese et al., "Effectiveness and Safety of a Novel Gel Dressing in the Management of Neuropathic Leg Ulcers in Diabetic Patients: A Prospective Double-Blind Randomized Trial", International Journal of Lower Extremity Wounds, Sep. 2009, 8(3): pp. 134-140.
Corsetti et al., "Topical Application of Dressing With Amino Acids Improves Cutaneous Wound Healing in Aged Rats", Acta Histochem, Sep. 2010, 112(5); pp. 497-507.
www.argonx.serverlet.com/media/prodotti/scheda/VULNAMIN_GEL_rcp.pdf, Mar. 11, 2014.
Michael F. McGuire, "Optimizing Wound Healing and Minimizing Scarring With Amino-Plex", http://www.woundcarenurses.org/uploads/7/6/6/7/7667574/amino-plex_info.pdf, Sep. 2, 2014.
Silvetti et al., "An Effective Method of Treating Long-Enduring Wounds and Ulcers by Topical Applications of Solutions of Nutrients", Journal of Dermatologic Surgery and Oncology, Jun. 1980, vol. 7(6), pp. 501-508.
Chirife et al., "In Vitro Study of Bacterial Growth Inhibition in Concentrated Sugar Solutions: Microbiological Basis for the Use of Sugar in Treating Infected Wounds", Antimicrobial Agents and Chemotherapy, vol. 23(5), May 1983, pp. 766-773.
Amino Acids, www.aminoacidsguide.com, Sep. 15, 2014.
Arata et al., "Effect of Topical Application of Glycine and Proline on Recalcitrant Leg Ulcers of Prolidase Deficiency", Archives of Dermatology, American Medical Association, U.S. vol. 122, 1986, pp. 626-627.
Bulstrode et al., "A prospective controlled trial of topical irrigation in the treatment of delayed cutaneous healing in human leg ulcers", Clinical Science, vol. 75, No. 6, 1988, pp. 637-340.
Silvetti et al., "Accelerated Wound Healing and Infection Control Through the Topical Application of Nutrients", Federation Proceedings, Bethesda, MD, U.S., vol. 40, No. 3, 1981, p. 922.
PCT/US2015/055476, International Search Report and Written Opinion, dated Feb. 9, 2016, 16 pages.
PCT/US2015/055476, International Preliminary Report on Patentability and Written Opinion of the International Searching Authority, dated May 4, 2017, pp. 1-9.

* cited by examiner

METHODS TO INHIBIT INFECTION DURING WOUND HEALING WITH TOPICAL COMPOSITIONS INCLUDING AMINO ACIDS

BACKGROUND

Field of the Invention

The present disclosure relates to methods that inhibit infection during wound healing by topical application of a single composition that contacts a wound for a period of time sufficient to initiate wound healing. Specifically, the present disclosure relates to the topical application of a single composition comprising an aqueous mixture of one or more amino acids that is applied to a wound site. The present disclosure also specifically relates to a topical application of a single composition comprising one or more powdered amino acids that forms a mixture with the exudate of a wound.

Description of Related Art

Wound healing is a complex metabolic process whereby the skin, or another organ-tissue, repairs itself after injury resulting from any of burns, mechanical trauma, surgery, pressure ulcers, and diabetic lesions. Classically, wound healing has been divided into four overlapping phases: hemostasis, inflammation, cellular proliferation, and cellular remodeling. Within minutes following injury, platelets aggregate at the wound site to form a fibrin clot that reduces active bleeding—hemostasis. During the inflammatory phase, bacteria and cellular debris, including necrotic tissue, are phagocytized and removed from the wound site by white blood cells. The cellular proliferation phase is characterized by angiogenesis, collagen deposition, granulation tissue formation, epithelialization, and wound contraction. During cellular remodeling, collagen is remodeled and re-aligned along lines of tension and apoptosis removes unnecessary cells. Nerve regeneration may begin as early as the cellular proliferation phase and continue throughout cellular remodeling to maturation of the regrown tissues at the wound site.

Bacterial infection of a wound is a major impediment to wound healing. Necrotic tissue at the wound site provides a culture medium for microbes that are frequently unresponsive to systemically administered antibiotics. Historically, it has been shown that honey, sugar, and molasses promote healing when placed in contact with a wound. The effect of various sucrose concentrations on the growth of pathogenic bacteria indicates that hyperosmotic concentrations, i.e., concentrations greater than that of the normal range of plasma osmolality in mammals, 285-295 mOsm/kg, inhibit or stress the growth of pathogenic bacteria (Chirife et al., 1983). The thermodynamic activity of water, ($a_w$), is inversely related to solute concentration; hence, high sucrose concentrations correspond to low activities of water, ($a_w$), associated with the inhibition of growth of the pathogenic bacteria. Similarly, concentrations of maltodextrin, ranging from 20% to 70% w/v, inhibit in-vitro bacterial growth when added to a growth medium (Silvetti, 2014).

Wound healing is slowed by poor perfusion of nutrients to the wound site, where they are needed for wound repair. Local hyperalimentation of wounds is accomplished by multiple topical applications including first and second irrigations of a viscose cellulose sponge covering the wound site (Viljanto et al., 1976). The first irrigating solution contains calcium chloride, sodium hydroxide, and a mixture of amino acids, where the mixture of amino acids is hypo-osmotic relative to plasma osmolarity, while the second irrigating solution contains a mixture of salts, vitamins, and glucose, where the glucose is also hypo-osmotic. Histochemical analyses, based on this method of local hyperalimentation, indicate increased activities of adenosine triphosphastase, aminopeptidase, and alkaline phosphatase that reflect increased synthesis and proliferative functions of granulation tissue cells in wound healing.

Multiple topical applications including the sequential irrigation a wound with a first solution of salts, followed by irrigation with a second solution of amino acids, where the second solution of amino acids is hyperosmotic relative to plasma osmolarity, and finally by covering the wound site with a maltodextrin powder can effectively treat wounds and ulcers (Silvetti, 1981).

A method of preventing infection can include applying solutions or powders of sucrose or maltodextrin to the wound site. Similarly, local hyperalimentation of a wound can include multiple topical applications of a wound covering, including first and second irrigations, where a first irrigating solution contains a hypo-osmotic mixture of amino acids and a second irrigating solution contains salts, vitamins, and a hypo-osmotic concentration of glucose. Wounds can also be treated by multiple topical application including the sequential irrigation of a wound with a first solution of salts, followed by a second irrigation with a second hyperosmotic solution of amino acids, and finally by covering the wound site with a maltodextrin powder.

SUMMARY

In view of the foregoing, the present disclosure may provide a method that inhibits infection during wound healing by topical application of a single composition that contacts a wound for a period of time to initiate wound healing, where the single composition may comprise a mixture of amino acids in the following proportional number of moles, plus or minus 5 percent: histidine monohydrochloride monohydrate, 9.743 mmol; isoleucine, 54.594 mmol; leucine, 109.264 mmol; lysine acetate, 21.402 mmol; methionine, 21.229 mmol; phenylalanine, 27.034 mmol; threonine, 29.062 mmol; tryptophan, 5.424 mmol; valine, 61.095 mmol; alanine, 50.321 mmol; arginine acetate, 28.227 mmol; aspartic acid, 54.582 mmol; glutamine, 76.100 mmol; glycine, 46.232 mmol; proline, 36.684 mmol; serine, 24.130 mmol; and tyrosine, 4.012 mmol. A sum of a number of moles of each of the amino acids may equal at least 120 mmol, when each of the number of moles of each of the amino acids is multiplied by a proportional factor of about 0.185. The sum of the number of moles of each of the amino acids, when mixed in one liter of water, may provide an osmolarity of at least 120 mmol/liter, to a total osmolarity of the single composition.

The present disclosure may also provide a method that inhibits infection during wound healing by topical application of a single composition that contacts a wound for a period of time to initiate wound healing, where the single composition may comprise a mixture of powdered amino acids in the following proportional number of moles, plus or minus 5 percent: histidine monohydrochloride monohydrate, 9.743 mmol; isoleucine, 54.594 mmol; leucine, 109.264 mmol; lysine acetate, 21.402 mmol; methionine, 21.229 mmol; phenylalanine, 27.034 mmol; threonine, 29.062 mmol; tryptophan, 5.424 mmol; valine, 61.095 mmol; alanine, 50.321 mmol; arginine acetate, 28.227 mmol; aspartic acid, 54.582 mmol; glutamine, 76.100 mmol; glycine, 46.232 mmol; proline, 36.684 mmol; serine, 24.130 mmol; and tyrosine, 4.012 mmol. The mixture of powdered amino acids may be mixed in an exudate in and around a wound site.

The present disclosure may further provide a method that inhibits infection during wound healing by topical application of a single composition that contacts a wound for a period of time to initiate wound healing, where the single composition may comprise one of the following amino acids: histidine; isoleucine; leucine; lysine; methionine; phenylalanine; threonine; valine; alanine; arginine; glutamine; glycine; proline; and serine. Each of the one of the following amino acids may provide an osmolarity of at least 120 mmol/liter, when mixed in one of: water, and an aqueous exudate in and around a wound site. The osmolarity of at least 120 mmol/liter is determined by a maximum aqueous solubility of each of the one of the following amino acids.

The present disclosure may yet further provide a method that inhibits infection during wound healing by topical application of a single composition that contacts a wound for a period of time to initiate wound healing, where the single composition may comprise one of the following amino acids: lysine; threonine; valine; alanine; arginine; proline; and serine. Each of the one of the following amino acids may provide a hyperosmotic osmolarity of at least 650 mmol/liter, when mixed in one of: water, and an aqueous exudate in and around a wound site. The hyperosmotic osmolarity of at least 650 mmol/liter may be determined by a maximum aqueous solubility of each of the one of the following amino acids.

The present disclosure may yet further provide a method that inhibits infection during wound healing by topical application of a single composition that contacts a wound for a period of time to initiate wound healing, where the single composition may comprise one of the following amino acids: lysine; alanine; arginine; proline; and serine. Each of the one of the following amino acids may provide a hyperosmotic osmolarity of at least 1000 mmol/liter, when mixed in one of: water, and an aqueous exudate in and around a wound site. The hyperosmotic osmolarity of at least 1000 mmol/liter may be determined by a maximum aqueous solubility of each of the one of the following amino acids.

The present disclosure may yet further provide a method that inhibits infection during wound healing by topical application of a single composition that contacts a wound for a period of time to initiate wound healing, where the single composition may comprise: at least two of the following amino acids: histidine; isoleucine; leucine; lysine; methionine; phenylalanine; threonine; tryptophan; valine; alanine; aspartic acid; arginine; aspartic acid; glutamine; glycine; proline; serine; and tyrosine, while excepting the pairs of aspartic acid-tryptophan, aspartic acid-tyrosine, and tryptophan-tyrosine, and the triplet of aspartic acid-tryptophan-tyrosine. At least two of the amino acids, excepting the pairs of aspartic acid-tryptophan, aspartic acid-tyrosine, and tryptophan-tyrosine, and the triplet of aspartic acid-tryptophan-tyrosine, may provide an osmolarity of at least 120 mmol/liter, when mixed in one of: water, and an aqueous exudate in and around a wound site. The osmolarity of at least 120 mmol/liter may be determined by a maximum aqueous solubility of each constituent of at least two of the amino acids.

DETAILED DESCRIPTION

As stated above, wound healing is a complex metabolic process whereby the skin, or another organ-tissue, repairs itself after injury. During the initial phase of hemostasis, platelets aggregate at the wound site to form a fibrin clot, which reduces bleeding and forms an anatomical barrier against entry by external pathogenic bacteria and fluid loss from interior tissues of the body.

However, this anatomical barrier to fluid loss is not absolute. Wound healing is frequently characterized by an exudate at the wound site, where the exudate includes water and plasma constituents. Driven by the pressure of interior tissues, fluid transfer results in the flow of exudate across the anatomical barrier to the exterior. The exudate may also result from osmosis, which draws water across the anatomical barrier to high concentrations of solutes applied to the exterior wound site.

Prior investigations have shown that high concentrations of sucrose or maltodextrin can inhibit bacterial growth. It has been hypothesized that low water activity, ($a_w$), which is inversely related to high concentrations of a dissolved solute, may inhibit the growth of the pathogenic bacteria (Chirife et al., 1983). Chemically, a low water activity, ($a_w$), may also be produced by high concentrations of solutes other than sucrose or maltodextrin. For example, a high concentration of one or more amino acids may also result in low water activity, ($a_w$). In another investigation, a total number of moles equal to about 120 mmol corresponds to a calculated osmolarity of 20% w/v of a maltodextrin that inhibits bacterial growth (Silvetti, 2014). Therefore, an aspect of the present disclosure may provide a single composition of an aqueous mixture of one or more amino acids having an osmolarity that inhibits infection when topically applied to a wound site.

When an aqueous exudate from a wound initially contacts dry particles of one or more powdered amino acids that are applied to a wound site, the particles may partially dissolve or fully dissolve to form a small volume of a nearly saturated or fully saturated solution. The concentrations of the partially dissolved or fully dissolved one or more amino acid particles in a small volume of solution are limited by the maximum solubilities of the one or more amino acids in water. These nearly saturated or saturated solutions of one or more amino acids may have an osmolarity that inhibits growth of pathogenic bacteria. Therefore, another aspect of the present disclosure may provide a composition comprising one or more powdered amino acids that are mixed with an exudate in or around a wound site to form an aqueous mixture having an osmolarity, which inhibits growth of bacteria.

Yet another aspect of the disclosure may provide for topical application of a single composition that contacts a wound to inhibit infection during wound healing for a period of time sufficient to initiate the wound healing, rather than multiple and sequential topical applications of different compositions of different solutions, or of a first composition of a solution and a second composition of a powder during a treatment. A topical application of a single composition to a wound site to inhibit infection during treatment is more efficient and less costly to the health care provider than multiple and sequential topical applications of different compositions during a treatment.

Nutrients are those components of food required to support metabolic life and growth of cells in a living organism. Organic nutrients include: proteins or the amino acids that make up proteins, carbohydrates, fats, and vitamins. Inorganic chemical compounds such as minerals, water, and oxygen are also considered nutrients. Vitamins and some minerals are considered micronutrients, requiring only trace amounts for good health.

A nutrient is characterized as indispensable if it cannot be produced within the body or cannot be produced in large enough quantities to satisfy the body's metabolic needs. Some nutrients are regarded as conditionally indispensable in certain cases, e.g., severe catabolic distress or prematurity in an infant, while other nutrients are characterized as dispensable, meaning they can be synthesized in the body.

Amino acids are either indispensable, conditionally indispensable, or dispensable. The indispensable amino acids consist of: histidine, isoleucine, leucine, lysine, methionine, phenylalanine, threonine, tryptophan, and valine. The conditionally indispensable amino acids may include: arginine, cysteine, glutamine, glycine, proline, and tyrosine, while the dispensable amino acids may include: alanine, asparagine, aspartic acid, glutamic acid, and serine. L-enantiomers of the amino acids with the exception of glycine, which lacks an asymmetric carbon atom, are used exclusively for protein synthesis in all life forms.

A primary function of carbohydrates is to provide energy for metabolic activity of the body. Carbohydrates include monosaccharides, disaccharides, and polysaccharides. Monosaccharides are the simplest carbohydrates in that they cannot be hydrolyzed, i.e., broken down, into smaller carbohydrates. The disaccharide, sucrose, comprises two monosaccharide units, glucose and fructose, linked together by a glycosidic bond. Similarly, many monosaccharide units, of the same type or of different types, are linked together by glycosidic bonds to form polysaccharides. Maltodextrin is an example of a polysaccharide consisting of D-glucose units linked by glycosidic bonds to form chains of variable length. In the presence of acid, such as that of gastric acids, the glycosidic bonds of disaccharides and polysaccharides are readily digested, allowing the resultant monosaccharides to be absorbed by the blood supply.

Chemically, fats are triesters of glycerol and any of several fatty acids. Fat is an important part of the diet, a structural component of cellular membranes, and necessary for many metabolic functions. There are two essential fatty acids: alpha-linolenic acid and linoleic acid.

Vitamins are organic compounds and indispensable nutrients that an organism requires in limited amounts to satisfy the body's metabolic needs. Vitamins are classified by their biological and chemical activity, and not their structure. Each vitamin may include a number of chemical compounds that show the biological activity associated with a particular vitamin. For example, vitamin A includes the chemical compounds of retinal, retinol, four carotenoids, and their derivatives. Retinyl palmitate, or vitamin A palmitate, is the ester of retinol and palmitic acid.

Mineral nutrients are the chemical compounds containing chemical elements, other than the four elements of carbon, hydrogen, nitrogen and oxygen found in most organic molecules. The term, "mineral nutrient", may be misleading because the substance to which it refers is a chemical compound, e.g., calcium glycerophosphate, which need not be an actual mineral. In addition to their role in the biochemical reactions of metabolism, the mineral nutrients play an important role in the body's electrolyte balance.

Therefore, yet another aspect of the disclosure may provide a topical application of a single composition comprising one or more nutrients at a wound site.

The present disclosure may describe a single composition that is topically applied to a wound to inhibit infection during wound healing.

The single composition may comprise a mixture, including one or more amino acids mixed in water, where a calculated total osmolarity of the one or more amino acids may equal at least 120 mmol/liter. Preferably, the calculated total osmolarity of the one or more amino acids in the single composition may equal a hyperosmotic mixture of at least 650 mmol/liter, and more preferably, the calculated total osmolarity of the one or more amino acids in the single composition may equal a hyperosmotic solution of at least 1000 mmol/liter. The single composition, above, may also comprise a mixture, including the one or more amino acids and a carbohydrate mixed in water, where a calculated osmolarity of the one or more amino acids is greater than a calculated osmolarity of the carbohydrate. The single composition, above, may further comprise at least one of: a number of moles of an essential fatty acid, a number of moles of a mixture of vitamins, and a number of moles of a mixture of mineral nutrients mixed in water, where each of the numbers of moles of the essential fatty acid, the mixture of vitamins, and the mixture of mineral nutrients is proportional to the total number of moles of the one or more amino acids mixed in water. The single composition, above, may yet further comprise at least one of: a number of moles of an amino acid derivative, a number of moles of a preservative, a number of moles of an emulsifier, and a number of moles of a hydrogel mixed in water, where each of the numbers of moles of the amino acid derivative, the preservative, the emulsifier, and the hydrogel is proportional to the total number of moles of the one or more amino acids mixed in water.

The single composition may also comprise a mixture, including one or more powdered amino acids, resulting in a hyperosmotic mixture of the one or more amino acids in an exudate in or around a wound site. The single composition, above, may also comprise a mixture, including the one or more powdered amino acids and a powdered carbohydrate, where the total number of moles of the one or more powdered amino acids is greater than and proportional to the number of moles of the powdered carbohydrate. The single composition, above, may further comprise at least one of: a number of moles of an essential fatty acid, a number of moles of a mixture of vitamins, and a number of moles of a mixture of mineral nutrients, where each of the numbers of moles of the essential fatty acid, the mixture of vitamins, and the mixture of mineral nutrients is proportional to the total number of moles of the one or more powdered amino acids. The single composition, above, may yet further comprise at least one of: a number of moles of an amino acid derivative and a number of moles of a preservative, where each of the numbers of moles of the amino acid derivative and the preservative is proportional to the total number of moles of the one or more powdered amino acids.

A. Amino Acids.

An exemplary single composition, to be topically applied at a wound site, may comprise a mixture of amino acids that inhibits infection and provides one or more nutrients. The recommended daily allowances of each of the indispensable amino acids vary with age and sex, during pregnancy and while lactating, with the presence or absence of disease or injury, and with prior nutritional state, e.g., starvation. Among the indispensable amino acids, the recommended daily allowance for leucine is highest, while the recommended daily allowance for tryptophan is lowest.

An exemplary single composition, to be topically applied at a wound site to inhibit bacterial infection and provide one or more nutrients, may comprise an aqueous mixture of amino acids that provides an osmolarity of at least 650 mOsm/liter. Assuming an ideal solution, a total osmolarity for a mixture of amino acids may be calculated, based on the sum of the molar concentrations of each of the dissolved amino acids in one liter of the aqueous mixture. Typically, calculations of osmolarity for ideal solutions assume low concentrations, i.e., less than about 500 mmol/liter, and further assume no electrostatic interactions among constituents of the aqueous mixture. Calculations of osmolarity may also reflect the degree of dissociation of amino acid salts, e.g., lysine acetate, into its two equivalents, lysine and acetate. Dissolution of some of the amino acids may be limited by their maximum solubilities in water; a quantity of an amino acid that is not dissolved, does not contribute to the total osmolarity. Any undissolved amino acids may be physically dispersed within the mixture as a colloidal suspension.

Alternatively, a calculated total osmolarity of an aqueous mixture of amino acids may approximate the measured total osmolality of the aqueous mixture of amino acids as measured by, for example, a membrane osmometer (VaPro Vapor Pressure Osmometer Unit, Model 5600, Wescor Biomedical Systems, Inc.). The membrane osmometer measures osmolality, i.e., mmol/kg of water or mOsm/kg of water, rather than osmolarity, i.e., mmol/liter of mixture or mOsm/liter of mixture. An osmolality measurement may be slightly greater than a calculated osmolarity by a few percent at body temperature. Hereinafter, a measured osmolality value, i.e., mmol/kg or mOsm/kg, may be considered an approximation of an osmolarity value that includes any effects relating to degrees of dissociation, maximum solubilities, and electrostatic interactions of constituents of an aqueous mixture.

An exemplary single composition, to be topically applied at a wound site to inhibit bacterial infection and provide one or more nutrients, may comprise an aqueous mixture of amino acids, including each of the indispensable amino acids and each of the following conditionally indispensable and dispensable amino acids, in one liter of water in the following proportional number of moles and equivalent weights, plus or minus 5 percent: histidine monohydrochloride monohydrate, 9.743 mmol and 2.042 g; isoleucine, 54.594 mmol and 7.157 g; leucine, 109.264 mmol and 14.332 g; lysine acetate, 21.402 mmol and 4.414 g; methionine, 21.229 mmol and 3.168 g; phenylalanine, 27.034 mmol and 4.466 g; threonine, 29.062 mmol and 3.462 g; tryptophan, 5.424 mmol and 1.108 g; valine, 61.095 mmol and 7.157 g; alanine, 50.321 mmol and 4.483 g; arginine acetate, 28.227 mmol and 6.612 g; aspartic acid, 54.582 mmol and 6.067 g; glutamine, 76.100 mmol and 11.121 g; glycine, 46.232 mmol and 3.471 g; proline, 36.684 mmol and 4.223 g; serine, 24.130 mmol and 2.536 g; and tyrosine, 4.012 mmol and 0.727 g. The total sums of the number of moles and the equivalent weights of each of the indispensable amino acids and each of the conditionally indispensable and dispensable amino acids, in the aqueous mixture, above, are 650.135 mmol and 86.546 g, plus or minus 5 percent, respectively.

However, when the total sum of the number of moles of each of the indispensable amino acids and each of the conditionally indispensable and dispensable amino acids, in the exemplary single composition, above, is mixed in one liter of water, the calculated total osmolarity of about 650 mmol/liter is less than that measured by the membrane osmometer, i.e., a measured average value of 689 mmol/kg.

The difference between the calculated total osmolarity and the measured total osmolality in the exemplary single composition may be partially explained by the dissociation of some of the amino acid salts. The calculated number of moles of lysine acetate, i.e., 21.402 mmol, in the aqueous mixture may, instead, contribute an additional about 21.4 mOsm/liter to the calculated total osmolarity, which reflects the dissociation of lysine acetate into its two lysine and acetate equivalents. Additionally, the calculated number of moles of arginine acetate, i.e., 28.227 mmol, in the aqueous mixture may, instead, contribute an additional about 28.2 mOsm/liter to the calculated total osmolarity, which reflects the dissociation of arginine acetate into arginine and acetate equivalents. Similarly, the calculated number of moles of histidine monohydrochloride monohydrate, i.e., 9.743 mmol, in the aqueous mixture may, instead, contribute more than 9.743 mOsm/liter to the calculated total osmolarity, which reflects an increase in the calculated osmolarity due to the dissociation of histidine monohydrochloride monohydrate into histidine and hydrochloride equivalents, and a decrease in the calculated osmolarity due to the non-ideal electrostatic effects of hydrochloride in water.

Furthermore, the maximum solubility of aspartic acid in water, i.e., 5.0 g/l, limits the calculated osmolarity of aspartic acid mixed in one liter of water to about 38 mOsm/liter. Therefore, of the calculated 6.067 g of aspartic acid mixed in the one liter of water, only about 5.0 g may dissolve, decreasing the calculated total osmolarity by about 8.0 mOsm/liter. The remaining about 1.07 g of undissolved aspartic acid may be dispersed as a colloidal suspension that does not contribute to the total calculated osmolarity. Similarly, the maximum solubility of tyrosine in water, i.e., 0.45 g/l, limits the osmolarity of tyrosine mixed in one liter of water to about 2.5 mOsm/liter. Therefore, of the calculated 0.727 g of tyrosine mixed in the one liter of water, only about 0.45 g may dissolve, decreasing the calculated total osmolarity by about 1.5 mOsm/liter. The remaining about 0.3 g of undissolved tyrosine may be dispersed as a colloidal suspension that does not contribute to the total calculated osmolarity.

Thus, when the effects reflecting the degree of dissociation and the maximum solubilities of the amino acids are accounted for in a calculation of the total osmolarity of an aqueous mixture of each of the indispensable amino acids and each of the conditionally indispensable and dispensable amino acids, the calculated total osmolarity, i.e., a hyperosmotic value of about 690.1 mOsm/liter, compares favorably with average membrane osmometer measurement of 689 mOsm/liter.

The total sums of the number of moles and the equivalent weights of each of the indispensable amino acids and each of the conditionally indispensable and dispensable amino acids in the aqueous mixture, above, may be varied by multiplying each of the number of moles and the equivalent weights by a proportional factor. A total number of moles, equaling about 120 mmol, corresponds to the calculated osmolarity of 20% w/v of maltodextrin that inhibits bacterial growth (Silvetti, 2014), based on a MW of about 1707 g/mol for the maltodextrin from membrane osmometer measurements. Hence, to obtain, for example, a total quantity of about 120 mmol of the aqueous mixture of amino acids in one liter of water, the number of moles of each of the indispensable amino acids and each of the conditionally indispensable and dispensable amino acids may be multiplied by a proportional factor of about 0.185, yielding a total equivalent weight of about 16.0 g. In this case, however, neither of the maximum solubilities for aspartic acid or tyrosine is exceeded and both of these amino acids will be dissolved in the aqueous mixture. Similarly, to obtain, for example, a total quantity of about 1000 mmol of the aqueous mixture of amino acids in one liter of water, the number of moles of each of the indispensable amino acids and each of the conditionally indispensable and dispensable amino acids may be multiplied by a proportional factor of about 1.538, yielding a total equivalent weight of about 133.148 g. In this case, however, the maximum solubilities of aspartic acid and tyrosine are exceeded, and will decrease the calculated total osmolarity of the aqueous mixture.

Another exemplary single composition, to be topically applied at a wound site to inhibit bacterial infection and provide one or more nutrients, may comprise an aqueous mixture of amino acids, including only the indispensable amino acids, in one liter of water, where the proportionality of each of the indispensable amino acids, one to the other, is the same as that for the aqueous mixture of amino acids of each of the indispensable amino acids and each of the conditionally indispensable and dispensable amino acids, described above, where the calculated total number of moles of the mixture of amino acids including only the indispensable amino acids is 650 mmol. This aqueous mixture of amino acids, including only the indispensable amino acids, may comprise the following proportional number of moles and equivalent weights, plus or minus 5 percent: histidine monohydrochloride monohydrate, 18.812 mmol and 3.941 g; isoleucine, 105.267 mmol and 13.810 g; leucine, 210.817 mmol and 27.653 g; lysine acetate, 41.300 mmol and 8.516 g; methionine, 40.966 mmol and 6.112 g; phenylalanine, 52.171 mmol and 8.616 g; threonine, 56.077 mmol and 6.679 g; tryptophan, 10.460 mmol and 2.137 g; and valine, 115.316 mmol and 13.810 g. The calculated total sums of the number of moles and the equivalent weights of each of the indispensable amino acids in this aqueous mixture are 651.186 mmol and 91.274 g, respectively.

The difference between the calculated total number of moles and a measured total osmolality in the exemplary single composition, above, may be partially determined by the dissociation of the calculated number of moles of lysine acetate, i.e., 41.300 mmol, in the aqueous mixture, which may contribute an additional about 41.3 mOsm/liter to the calculated total osmolarity, reflecting the dissociation of lysine acetate into its two lysine and acetate equivalents. Similarly, the calculated number of moles of histidine monohydrochloride monohydrate, i.e., 18.812 mmol, in the aqueous mixture may, instead, contribute more than 18.812 mOsm/liter to the calculated total osmolarity, which reflects an increase in the calculated osmolarity due to the dissociation of histidine monohydrochloride monohydrate into its histidine and hydrochloride equivalents and a decrease in the calculated osmolarity due to the non-ideal electrostatic effects of hydrochloride in water.

Furthermore, the maximum solubility of leucine in water, i.e., 22.4 g/l, limits the osmolarity of leucine mixed in one liter of water to about 170.8 mOsm/liter. Therefore, of the calculated 27.653 g of leucine mixed in the one liter of water, only about 22.4 g may dissolve, decreasing the calculated total osmolarity by about 40.0 mOsm/liter. The remaining about 5.25 g of undissolved leucine may be dispersed as a colloidal suspension that does not contribute to the total calculated osmolarity.

Again, the total sums of the number of moles and the equivalent weights of each of the indispensable amino acids in the aqueous mixture, above, may be varied by multiplying each of the number of moles and the equivalent weights by a proportional factor. To obtain, for example, a total quantity of about 120 mmol of the aqueous mixture of amino acids in one liter of water, the number of moles of each of the indispensable amino acids may be multiplied by a proportional factor of about 0.185, yielding a total equivalent weight of about 16.9 g. In this case, however, the maximum solubility of leucine is not exceeded and the about 5.1 g of leucine will be dissolved in the aqueous mixture. Similarly, to obtain, for example, a total quantity of about 1000 mmol of the aqueous mixture of amino acids in one liter of water, the number of moles of each of the indispensable amino acids may be multiplied by a proportional factor of about 1.538, yielding a total equivalent weight of about 140.4 g. In this case, however, the maximum solubility of leucine is further exceeded, and will decrease the calculated total osmolarity of the aqueous mixture.

Yet another exemplary single composition, to be topically applied at a wound site to inhibit bacterial infection and provide one or more nutrients, may comprise an aqueous mixture of amino acids, including each of the indispensable amino acids and at least one of the following conditionally indispensable and dispensable amino acids, in one liter of water. The proportionality of the at least one of the following conditionally indispensable and dispensable amino acids to the amounts of the indispensable amino acids may be the same as that of each corresponding one of the conditionally indispensable and dispensable amino acids to the amounts of indispensable amino acids in the aqueous mixture of amino acids, including each of the indispensable amino acids and each of the conditionally indispensable and dispensable amino acids, described above.

For example, based on the proportions of the aqueous mixture of amino acids, including each of the indispensable amino acids and each of the conditionally indispensable and dispensable amino acids, described above, an aqueous mixture of amino acids including one of the conditionally indispensable acids, e.g., glutamine, may comprise the following proportional number of moles and equivalent weights, plus or minus 5 percent: histidine monohydrochloride monohydrate, 9.743 mmol and 2.042 g; isoleucine, 54.594 mmol and 7.157 g; leucine, 109.264 mmol and 14.332 g; lysine acetate, 21.402 mmol and 4.414 g; methionine, 21.229 mmol and 3.168 g; phenylalanine, 27.034 mmol and 4.466 g; threonine, 29.062 mmol and 3.462 g; tryptophan, 5.424 mmol and 1.108 g; valine, 61.095 mmol and 7.157 g; and glutamine, 76.100 mmol and 11.121 g. The total sums of the number of moles and the equivalent weights of each of the indispensable amino acids and one of the conditionally indispensable amino acids, i.e., glutamine, in the aqueous mixture, above, are 414.947 mmol and 58.427 g, plus or minus 5 percent, respectively. To obtain, for example, a total quantity of about 650 mmol of the aqueous mixture of amino acids in one liter of water, the number of moles of each of the indispensable amino acids and the one conditionally indispensable amino acid, glutamine, may be multiplied by a proportional factor of about 1.566, yielding a total equivalent weight of about 91.497 g. Similarly, to obtain, for example, a total quantity of about 120 mmol of the aqueous mixture of amino acids in one liter of water, the number of moles of each of the indispensable amino acids and the one conditionally indispensable amino acid, glutamine, may be multiplied by a proportional factor of about 0.289, yielding a total equivalent weight of about 16.885 g. Yet again, to obtain, for example, a total quantity of about 1000 mmol of the aqueous mixture of amino acids in one liter of water, the number of moles of each of the indispensable amino acids and the one conditionally indispensable amino acid, glutamine, may be multiplied by a proportional factor of about 2.410, yielding a total equivalent weight of about 140.81 g.

Yet another exemplary single composition, to be topically applied at a wound site to inhibit bacterial infection and provide one or more nutrients, may comprise an aqueous mixture of one or more of each of the following amino acids: histidine; isoleucine; leucine; lysine; methionine; phenylalanine; threonine; valine; alanine; arginine; glutamine; glycine; proline; and serine, that provides a calculated osmolarity of at least 120 mOsm/liter, based on the respective maximum solubilities of each of the amino acids, above. That is, each one of the amino acids, above, may dissolve in water to produce a calculated osmolarity of at least 120 mOsm/liter, while a combination of two or more of the amino acids, above, may also dissolve in water to produce a calculated osmolarity of at least 120 mOsm/liter. The maximum aqueous solubilities of the amino acids are: histidine, 41.6 g/liter; isoleucine, 41.2 g/liter; leucine, 22.4 g/liter; lysine, 1500 g/liter; methionine, 53.7 g/liter; phenylalanine, 27 g/liter; threonine, 90 g/liter; valine, 85 g/liter; alanine, 166.5 g/liter; arginine, 148.7 g/liter; glutamine, 35 g/liter; glycine, 25 g/liter; proline, 1623 g/liter; and serine, 250 g/liter. Aspartic acid with a maximum solubility of 5.0 g/liter cannot provide a calculated osmolarity of 120 mOsm/liter. Similarly, tryptophan with a maximum solubility of 11.4 g/liter and tyrosine with a maximum solubility of 0.45 g/liter cannot provide a calculated osmolarity of 120 mOsm/liter.

Yet another exemplary single composition, to be topically applied at a wound site to inhibit bacterial infection and provide one or more nutrients, may comprise an aqueous mixture of one or more of each of the following amino acids: lysine; threonine; valine; alanine; arginine; proline; and serine, that provides a calculated osmolarity of at least 650 mOsm/liter, based on the respective maximum solubilities of each of the amino acids, above. That is, each one of the amino acids, above, may dissolve in water to produce a calculated osmolarity of at least 650 mOsm/liter, while a combination of two or more of the amino acids, above, may also dissolve in water to produce a calculated osmolarity of at least 650 mOsm/liter.

Yet another exemplary single composition, to be topically applied at a wound site to inhibit bacterial infection and provide one or more nutrients, may comprise an aqueous mixture of one or more of each of the following amino acids, including: lysine; alanine; arginine; proline; and serine, that provides a calculated osmolarity of at least 1000 mOsm/liter, based on the respective solubilities of each of the amino acids, above. That is, each one of the amino acids, above, may dissolve in water to produce a calculated osmolarity of at least 1000 mOsm/liter, while a combination of two or more of the amino acids, above, may also dissolve in water to produce a calculated osmolarity of at least 1000 mOsm/liter.

Yet another exemplary single composition, to be topically applied at a wound site to inhibit bacterial infection and provide two or more nutrients, may comprise an aqueous mixture of two or more of each of the amino acids: histidine; isoleucine; leucine; lysine; methionine; phenylalanine; threonine; tryptophan; valine; alanine; aspartic acid; arginine; aspartic acid; glutamine; glycine; proline; serine; and tyrosine, excepting the pairs of aspartic acid-tryptophan, aspartic acid-tyrosine, and tryptophan-tyrosine, that provides a calculated osmolarity of at least 120 mOsm/liter, based on the respective maximum solubilities of each of the amino acids, above. That is, each possible pair of the amino acids, above, excepting the pairs of aspartic acid-tryptophan, aspartic acid-tyrosine, and tryptophan-tyrosine may dissolve in water to produce a calculated osmolarity of at least 120 mOsm/liter. Similarly, an aqueous mixture of three or more of the amino acids, excepting the triplet of aspartic acid-tryptophan-tyrosine, may provide a calculated osmolarity of at least 120 mOsm/liter, based on the maximum solubilities of the amino acids, above.

An exemplary single composition, to be topically applied at a wound site to inhibit bacterial infection and provide one or more nutrients, may comprise a mixture of powdered amino acids, including each of the indispensable amino acids and each of the following conditionally indispensable and dispensable amino acids, in the following proportional number of moles and equivalent weights, plus or minus 5 percent: histidine monohydrochloride monohydrate, 9.743 mmol and 2.042 g; isoleucine, 54.594 mmol and 7.157 g; leucine, 109.264 mmol and 14.332 g; lysine acetate, 21.402 mmol and 4.414 g; methionine, 21.229 mmol and 3.168 g; phenylalanine, 27.034 mmol and 4.466 g; threonine, 29.062 mmol and 3.462 g; tryptophan, 5.424 mmol and 1.108 g; valine, 61.095 mmol and 7.157 g; alanine, 50.321 mmol and 4.483 g; arginine acetate, 28.227 mmol and 6.612 g; aspartic acid, 54.582 mmol and 6.067 g; glutamine, 76.100 mmol and 11.121 g; glycine, 46.232 mmol and 3.471 g; proline, 36.684 mmol and 4.223 g; serine, 24.130 mmol and 2.536 g; and tyrosine, 4.012 mmol and 0.727 g. The total sums of the number of moles and the equivalent weights of each of the powdered indispensable amino acids and each of the powdered conditionally indispensable and dispensable amino acids, above, are 650.135 mmol and 86.546 g, plus or minus 5 percent, respectively.

Again, the total sums of the number of moles and the equivalent weights of each of the powdered indispensable amino acids and each of the powdered conditionally indispensable and dispensable amino acids, above, may be varied by multiplying each of the number of moles and the equivalent weights by a proportional factor. To obtain, for example, a total quantity of about 28.35 g, i.e., about one ounce, of the powdered mixture of amino acids, the number of moles of each of the powdered indispensable amino acids and each of the powdered conditionally indispensable and dispensable amino acids may be multiplied by a proportional factor of about 0.328.

Another exemplary single composition, to be topically applied at a wound site to inhibit bacterial infection and provide one or more nutrients, may comprise a powdered mixture of amino acids, including only the powdered indispensable amino acids, where the proportionality of each of the powdered indispensable amino acids, one to the other, is the same as that for the powdered mixture of powdered amino acids, including each of the powdered indispensable amino acids and each of the powdered conditionally indispensable and dispensable amino acids, described above. This powdered mixture of amino acids, including only the powdered indispensable amino acids, may comprise the following proportional number of moles and equivalent weights, plus or minus 5 percent: histidine monohydrochloride monohydrate, 18.812 mmol and 3.941 g; isoleucine, 105.267 mmol and 13.810 g; leucine, 210.817 mmol and 27.653 g; lysine acetate, 41.300 mmol and 8.516 g; methionine, 40.966 mmol and 6.112 g; phenylalanine, 52.171 mmol and 8.616 g; threonine, 56.077 mmol and 6.679 g; tryptophan, 10.460 mmol and 2.137 g; and valine, 115.316 mmol and 13.810 g. The calculated total sums of the number of moles and the equivalent weights of each of the powdered indispensable amino acids in the powdered mixture of amino acids are 651.186 mmol and 91.274 g, respectively.

Again, the total sums of the number of moles and the equivalent weights of each of the powdered indispensable amino acids, above, may be varied by multiplying each of the number of moles and the equivalent weights by a proportional factor. To obtain, for example, a total quantity of about 28.35 g, i.e., about one ounce, of the powdered mixture of amino acids, the number of moles of each of the powdered indispensable amino acids may be multiplied by a proportional factor of about 0.311.

Yet another exemplary single composition, to be topically applied at a wound site to inhibit bacterial infection and provide one or more nutrients, may comprise a powdered mixture of amino acids, including each of the powdered indispensable amino acids and at least one of the following powdered conditionally indispensable and dispensable amino acids. The proportionality of the at least one of the following conditionally indispensable and dispensable amino acids to the amounts of the indispensable amino acids may be the same as that of each corresponding one of the conditionally indispensable and dispensable amino acids to the amounts of indispensable amino acids in the powdered mixture of amino acids, including each of the powdered indispensable amino acids and each of the powdered conditionally indispensable and dispensable amino acids, described above.

For example, based on the proportions of the powdered mixture of amino acids, including each of the powdered indispensable amino acids and each of the powdered conditionally indispensable and dispensable amino acids, described above, a powdered mixture of amino acids including one of the powdered conditionally indispensable acids, e.g., glutamine, may comprise the following proportional number of moles and equivalent weights, plus or minus 5 percent: histidine monohydrochloride monohydrate, 9.743 mmol and 2.042 g; isoleucine, 54.594 mmol and 7.157 g; leucine, 109.264 mmol and 14.332 g; lysine acetate, 21.402 mmol and 4.414 g; methionine, 21.229 mmol and 3.168 g; phenylalanine, 27.034 mmol and 4.466 g; threonine, 29.062 mmol and 3.462 g; tryptophan, 5.424 mmol and 1.108 g; valine, 61.095 mmol and 7.157 g; and glutamine, 76.100 mmol and 11.121 g. The total sums of the number of moles and the equivalent weights of each of the indispensable amino acids and one of the conditionally indispensable amino acids, i.e., glutamine, in the powdered mixture, above, are 414.947 mmol and 58.427 g, plus or minus 5 percent, respectively. To obtain, for example, a total quantity of about 28.35 g, i.e., about one ounce, of the powdered mixture of amino acids, above, the number of moles of each of the indispensable amino acids and the one conditionally indispensable amino acid, glutamine, may be multiplied by a proportional factor of about 0.485.

Yet another exemplary single composition, to be topically applied at a wound site to inhibit bacterial infection and provide one or more nutrients, may comprise a powdered mixture of one or more of each of the following amino acids: histidine; isoleucine; leucine; lysine; methionine; phenylalanine; threonine; valine; alanine; arginine; glutamine; glycine; proline; and serine, that may provide a calculated osmolarity of at least 120 mOsm/liter when dissolved in an aqueous exudate of a wound, based on the respective maximum solubilities of each of the amino acids, above, in water. That is, each one of the powdered amino acids, above, may dissolve in the aqueous exudate to produce a calculated osmolarity of at least 120 mOsm/liter, while a combination of two or more of the powdered amino acids, above, may also dissolve in the aqueous exudate to produce a calculated osmolarity of at least 120 mOsm/liter.

Any of the single compositions of one or more powdered amino acids, above, may comprise a sterile, non-pyrogenic powder of the powdered mixture of the amino acids that may be topically applied to a wound site to inhibit bacterial infection and provide one or more nutrients during wound healing. The sterile, non-pyrogenic powder of the single composition may comprise micronized particles, i.e., ranging from 75 microns to 250 microns in average diameter, that dissolve or are dispersed as a colloidal suspension in an exudate from the wound. When the exudate initially contacts the sterile, non-pyrogenic powder of the composition, particulates of the amino acids may dissolve or partially dissolve, forming small volumes of nearly saturated or saturated concentrations that are limited by the maximum solubilities of each of the amino acids in the exudate. These nearly saturated or saturated concentrations of each of the amino acids in the mixture may be summed, providing a total osmolarity that may inhibit growth of pathogenic bacteria during wound healing. The sterile, non-pyrogenic powder of the single composition may also be applied to the wound at the caregiver or patient's prerogative, i.e., pro re nata, as exudate is discharged from the wound during the time course of wound healing.

B. Carbohydrate

A single composition, to be topically applied at a wound site to inhibit infection and provide one or more nutrients, may comprise a mixture of amino acids and a carbohydrate, where a sum of the number of moles of each of the amino acids is greater than and proportional to the number of moles of the carbohydrate. The proportion of the sum of the number of moles of the mixture of amino acids to the number of moles of the carbohydrate may be about 5.40 moles of the mixture of amino acids to 1.00 mole of carbohydrate. Preferably, the proportion of the sum of the number of moles of the mixture of amino acids to the number of moles of the carbohydrate may be about 2.70 moles of the mixture of amino acids to 1.00 mole of the carbohydrate. The carbohydrate may comprise one of: D-glucose, sucrose, and a maltodextrin. Each of D-glucose, sucrose, and maltodextrin may be readily soluble or dispersed in water and may not dissociate to any appreciable degree in water at a neutral pH.

Measured osmolalities of 2.054475 g of a maltodextrin with a dextrose equivalent (DE) of 10 in 10 g of water yield an average value of 120.33 mmol/kg, which gives a calculated average MW of 1707.4 g/mol.

An exemplary single composition, to be topically applied at a wound site to inhibit bacterial infection and provide one or more nutrients, may comprise an aqueous mixture of amino acids, including each of the indispensable amino acids and each of the following conditionally indispensable and dispensable amino acids, and a carbohydrate in one liter of water in the following proportional number of moles and equivalent weights, plus or minus 5 percent: histidine monohydrochloride monohydrate, 9.743 mmol and 2.042 g; isoleucine, 54.594 mmol and 7.157 g; leucine, 109.264 mmol and 14.332 g; lysine acetate, 21.402 mmol and 4.414 g; methionine, 21.229 mmol and 3.168 g; phenylalanine, 27.034 mmol and 4.466 g; threonine, 29.062 mmol and 3.462 g; tryptophan, 5.424 mmol and 1.108 g; valine, 61.095 mmol and 7.157 g; alanine, 50.321 mmol and 4.483 g; arginine acetate, 28.227 mmol and 6.612 g; aspartic acid, 54.582 mmol and 6.067 g; glutamine, 76.100 mmol and 11.121 g; glycine, 46.232 mmol and 3.471 g; proline, 36.684 mmol and 4.223 g; serine, 24.130 mmol and 2.536 g; and tyrosine, 4.012 mmol and 0.727 g; and one of: D-glucose, 120.33 mmol and 21.679 g; sucrose, 120.33 mmol and 41.186 g; and maltodextrin, 120.33 mmol and 205.45 g. The total sum of the number of moles of each of the indispensable amino acids and each of the conditionally indispensable and dispensable amino acids in the aqueous mixture, above, is 650.135 mmol, plus or minus 5 percent, while the sum of the number of moles of any of the carbohydrates is 120.33 mmol, plus or minus 5 percent, giving a proportionality of about 5.40 between the sum of the number of moles of the mixture of amino acids to the number of moles of the carbohydrate.

When the sum of the number of moles of each of the indispensable amino acids and each of the conditionally indispensable and dispensable amino acids in the aqueous mixture, above, is about 120 mmol, the proportional number of moles of the carbohydrate may be about 22.22 mmol, giving a proportionality of about 5.40 between the sum of the number of moles of the mixture of amino acids to the number of moles of the carbohydrate. Similarly, when the sum of the number of moles of each of the indispensable amino acids and each of the conditionally indispensable and dispensable amino acids in the aqueous mixture, above, is about 1000 mmol, the proportional number of moles of the carbohydrate may be about 185.19 mmol, giving a proportionality of about 5.40 between the sum of the number of moles of the mixture of amino acids to the number of moles of the carbohydrate.

Another exemplary single composition, to be topically applied at a wound site to inhibit bacterial infection and provide one or more nutrients, may comprise an aqueous mixture of amino acids, including only the indispensable amino acids, and a carbohydrate in one liter of water, in the following proportional number of moles and equivalent weights, plus or minus 5 percent: histidine monohydrochloride monohydrate, 18.812 mmol and 3.941 g; isoleucine, 105.267 mmol and 13.810 g; leucine, 210.817 mmol and 27.653 g; lysine acetate, 41.300 mmol and 8.516 g; methionine, 40.966 mmol and 6.112 g; phenylalanine, 52.171 mmol and 8.616 g; threonine, 56.077 mmol and 6.679 g; tryptophan, 10.460 mmol and 2.137 g; and valine, 115.316 mmol and 13.810 g; and one of: D-glucose, 120.33 mmol and 21.679 g; sucrose, 120.33 mmol and 41.186 g; and maltodextrin, 120.33 mmol and 205.45 g. The total sum of the number of moles of each of the indispensable amino acids, above, is 651.186 mmol, plus or minus 5 percent, while the sum of the number of moles of any of the carbohydrates is 120.33 mmol, plus or minus 5 percent, giving a proportionality of about 5.40 between the sum of the number of moles of the mixture of amino acids to the number of moles of the carbohydrate.

When the sum of the number of moles of each of the indispensable amino acids in the aqueous mixture, above, is about 120 mmol, the proportional number of moles of the carbohydrate may be about 22.22 mmol, giving a proportionality of about 5.40 between the sum of the number of moles of the mixture of amino acids to the number of moles of the carbohydrate. Similarly, when the sum of the number of moles of each of the indispensable amino acids in the aqueous mixture, above, is about 1000 mmol, the proportional number of moles of the carbohydrate may be about 185.19 mmol, giving a proportionality of about 5.40 between the sum of the number of moles of the mixture of amino acids to the number of moles of the carbohydrate.

Yet another exemplary single composition, to be topically applied at a wound site to inhibit bacterial infection and provide one or more nutrients, may comprise an aqueous mixture of amino acids, including each of the indispensable amino acids and at least one of the following conditionally indispensable and dispensable amino acids, and a carbohydrate in one liter of water. The proportionality of the at least one of the following conditionally indispensable and dispensable amino acids to the amounts of the indispensable amino acids may be the same as that of each corresponding one of the conditionally indispensable and dispensable amino acids to the amounts of indispensable amino acids in the aqueous mixture of amino acids, including each of the indispensable amino acids and each of the conditionally indispensable and dispensable amino acids, described above.

For example, based on the proportions of the aqueous mixture of amino acids, including each of the indispensable amino acids and each of the conditionally indispensable and dispensable amino acids, described above, an aqueous mixture of amino acids including one of the conditionally indispensable acids, e.g., glutamine, and a carbohydrate may comprise the following proportional number of moles and equivalent weights, plus or minus 5 percent: histidine monohydrochloride monohydrate, 9.743 mmol and 2.042 g; isoleucine, 54.594 mmol and 7.157 g; leucine, 109.264 mmol and 14.332 g; lysine acetate, 21.402 mmol and 4.414 g; methionine, 21.229 mmol and 3.168 g; phenylalanine, 27.034 mmol and 4.466 g; threonine, 29.062 mmol and 3.462 g; tryptophan, 5.424 mmol and 1.108 g; valine, 61.095 mmol and 7.157 g; glutamine, 76.100 mmol and 11.121 g; and one of: D-glucose, 76.842 mmol and 13.844 g; sucrose, 76.842 mmol and 26.303 g; and maltodextrin, 76.842 mmol and 131.200 g. The total sum of the number of moles of each of the indispensable amino acids and one of the conditionally indispensable amino acids, i.e., glutamine, in the aqueous mixture, above, is 414.947.

To obtain, for example, a total quantity of about 650 mmol of the aqueous mixture of amino acids in one liter of water, the number of moles of each of the indispensable amino acids and the one conditionally indispensable amino acid, glutamine, may be multiplied by a proportional factor of about 1.566. Similarly, to obtain, for example, a total quantity of about 120 mmol of the aqueous mixture of amino acids in one liter of water, the number of moles of each of the indispensable amino acids and the one conditionally indispensable amino acid, glutamine, may be multiplied by a proportional factor of about 0.289. Yet again, to obtain, for example, a total quantity of about 1000 mmol of the aqueous mixture of amino acids in one liter of water, the number of moles of each of the indispensable amino acids and the one conditionally indispensable amino acid, glutamine, may be multiplied by a proportional factor of about 2.410.

When the sum of the number of moles of each of the indispensable amino acids and the one conditionally indispensable amino acid, glutamine, in the aqueous mixture, above, is proportionately adjusted to about 120 mmol, the proportional number of moles of the carbohydrate may be about 22.22 mmol, giving a proportionality of about 5.40 between the sum of the number of moles of the mixture of amino acids to the number of moles of the carbohydrate. In addition, when the sum of the number of moles of each of the indispensable amino acids and the one conditionally indispensable amino acid, glutamine, in the aqueous mixture, above, is proportionately adjusted to about 650 mmol, the proportional number of moles of carbohydrate may be about 120 mmol, giving a proportionality of about 5.40 between the sum of the number of moles of the mixture of amino acids to the number of moles of the carbohydrate. Similarly, when the sum of the number of moles of each of the indispensable amino acids and the one conditionally indispensable amino acid, glutamine, in the aqueous mixture is proportionately adjusted to about 1000 mmol, the proportional number of moles of the carbohydrate may be about 185.19 mmol, giving a proportionality of about 5.40 between the sum of the number of moles of the mixture of amino acids to the number of moles of the carbohydrate.

Yet another exemplary single composition, to be topically applied at a wound site to inhibit bacterial infection and provide one or more nutrients, may comprise an aqueous mixture of one or more of each of the following amino acids: histidine; isoleucine; leucine; lysine; methionine; phenylalanine; threonine; valine; alanine; arginine; glutamine; glycine; proline; and serine, that provides a calculated osmolarity of at least 120 mOsm/liter, based on their respective maximum solubilities; and a carbohydrate including one of: D-glucose; sucrose; and maltodextrin that may provide a calculated osmolarity giving a proportionality of about 5.40 between the sum of the at least 120 mmol of the aqueous mixture of amino acids to the number of moles of the carbohydrate.

Yet another exemplary single composition, to be topically applied at a wound site to inhibit bacterial infection and provide one or more nutrients, may comprise an aqueous mixture of one or more of each of the following amino acids: lysine; threonine; valine; alanine; arginine; proline; and serine, that provides a calculated osmolarity of at least 650 mOsm/liter, based on their respective maximum solubilities; and a carbohydrate including one of: D-glucose; sucrose; and maltodextrin, that may provide a calculated osmolarity giving a proportionality of about 5.40 between the sum of the at least 650 mmol of the aqueous mixture of amino acids to the number of moles of the carbohydrate.

Yet another exemplary single composition, to be topically applied at a wound site to inhibit bacterial infection and provide one or more nutrients, may comprise an aqueous mixture of one or more of each of the following amino acids: lysine; alanine; arginine; proline; and serine, that provides a calculated osmolarity of at least 1000 mOsm/liter, based on their respective maximum solubilities; and a carbohydrate including one of: D-glucose; sucrose; and maltodextrin, that may provide a calculated osmolarity giving a proportionality of about 5.40 between the sum of the at least 1000 mmol of the aqueous mixture of amino acids to the number of moles of the carbohydrate.

Yet another exemplary single composition, to be topically applied at a wound site to inhibit bacterial infection and provide one or more nutrients, may comprise an aqueous mixture of two or more of the following amino acids: histidine; isoleucine; leucine; lysine; methionine; phenylalanine; threonine; tryptophan; valine; alanine; aspartic acid; arginine; aspartic acid; glutamine; glycine; proline; serine; and tyrosine, excepting the pairs of aspartic acid-tryptophan, aspartic acid-tyrosine, and tryptophan-tyrosine, and the triplet of aspartic acid-tryptophan-tyrosine, that provides a calculated osmolarity of at least 120 mOsm/liter, based on their respective maximum solubilities; and a carbohydrate including one of: D-glucose; sucrose; and maltodextrin, that may provide a calculated osmolarity giving a proportionality of about 5.40 between the sum of the at least 120 mmol of the aqueous mixture of amino acids to the number of moles of the carbohydrate.

An exemplary single composition, to be topically applied at a wound site to inhibit bacterial infection and provide one or more nutrients, may comprise a mixture of powdered amino acids, including each of the indispensable amino acids and each of the conditionally indispensable and dispensable amino acids, described above, and a powdered carbohydrate, where the total sum of the number of moles of each of the indispensable amino acids and each of the conditionally indispensable and dispensable amino acids in the powdered mixture, above, is 650.135 mmol, plus or minus 5 percent, while the sum of the number of moles of any of the carbohydrates is 120.33 mmol, plus or minus 5 percent, giving a proportionality of about 5.40 between the sum of the number of moles of the mixture of amino acids to the number of moles of the carbohydrate. Again, the total sums of the number of moles and the equivalent weights of each of the powdered indispensable amino acids, each of the conditionally indispensable and dispensable amino acids, and the carbohydrate, above, may be varied by multiplying each of the number of moles and the equivalent weights by a proportional factor.

Another exemplary single composition, to be topically applied at a wound site to inhibit bacterial infection and provide one or more nutrients, may comprise a powdered mixture of amino acids, including only the indispensable amino acids, described above, and a powdered carbohydrate, where the total sum of the number of moles of each of the indispensable amino acids and each of the conditionally indispensable and dispensable amino acids in the powdered mixture, above, is 651.186 mmol, plus or minus 5 percent, while the sum of the number of moles of any of the carbohydrates is 120.33 mmol, plus or minus 5 percent, giving a proportionality of about 5.41 between the sum of the number of moles of the mixture of amino acids to the number of moles of the carbohydrate. Again, the total sums of the number of moles and the equivalent weights of each of the powdered indispensable amino acids, each of the powdered conditionally indispensable and dispensable amino acids, and the powdered carbohydrate, above, may be varied by multiplying each of the number of moles and the equivalent weights by a proportional factor.

Yet another exemplary single composition, to be topically applied at a wound site to inhibit bacterial infection and provide one or more nutrients, may comprise a powdered mixture of amino acids, including each the indispensable amino acids and at least one of the conditionally indispensable and dispensable amino acids, described above, and a powdered carbohydrate, where the total sum of the number of moles of each of the indispensable amino acids and the at least one of the conditionally indispensable and dispensable amino acids is proportionately greater than the number of moles of the powdered carbohydrate by a proportional factor of 5.40.

Yet another exemplary single composition, to be topically applied at a wound site to inhibit bacterial infection and provide one or more nutrients, may comprise a powdered mixture of one or more of each of the following amino acids: histidine; isoleucine; leucine; lysine; methionine; phenylalanine; threonine; valine; alanine; arginine; glutamine; glycine; proline; and serine, that provides a calculated osmolarity of at least 120 mmol/liter when dissolved in an aqueous exudate of a wound; and a powdered carbohydrate including one of: D-glucose; sucrose; and maltodextrin that may provide a calculated osmolarity giving a proportionality of about 5.40 between the sum of the at least 120 mmol of the aqueous mixture of amino acids to the number of moles of the carbohydrate.

C. Fatty Acids, Vitamins, and Mineral Nutrients

A single composition, to be topically applied at a wound site to inhibit infection and provide one or more, may comprise a mixture of: amino acids; and another mixture of fatty acids, vitamins, and mineral nutrients, where a sum of the number of moles of the mixture of amino acids is proportional to sums of the number of moles and equivalent weights of each of the constituents of the another mixture of fatty acids, vitamins, and mineral nutrients.

When the sum of the number of moles in any of the mixtures of aqueous amino acids or powdered amino acids, described above, is 650 mmol, the another mixture of fatty acids, vitamins, and mineral nutrients in the single composition, directly above, may comprise the following proportional number of moles and equivalent weights, plus or minus 5 percent: one of: alpha-linolenic acid, 47.836 mmol and 13.319 g; linoleic acid, 47.494 mmol and 13.319 g; and a combination of 23.918 mmol and 6.660 g of alpha-linolenic acid and 23.747 mmol and 6.660 g of linoleic acid; vitamin A palmitate, 2.617 μmol and 1.374 mg; vitamin D3 (cholecalciferol), 0.013 μmol and 0.0050 mg; vitamin E (alpha tocopherol), 23.35 μmol and 10.057 mg; pantothenic acid (vitamin B5), 45.567 μmol and 9.990 mg; and zinc sulfate, 61.866 μmol and 9.990 mg. The another mixture of fatty acids, vitamins, and mineral nutrients may further comprise the following proportional number of moles and equivalent weights, plus or minus 5 percent: vitamin C (ascorbic acid), 340.321 μmol and 59.937 mg; folic acid, 0.905 μmol and 0.400 mg; thiamine hydrochloride, 5.647 μmol and 1.498 mg; riboflavin, 4.512 μmol and 1.698 mg; niacinamide, 163.602 μmol and 19.979 mg; vitamin B6, 13.473 μmol and 3.30 mg; vitamin B12 (cyanocobalamin), 0.004 μmol and 0.0060 mg; biotin, 1.227 μmol and 0.300 mg; vitamin K1 (phytonadione), 0.089 μmol and 0.040 mg; choline bitartrate, 706.433 μmol and 75.590 mg; potassium chloride, 8.040 mmol and 599.373 mg; sodium citrate, 2.146 mmol and 459.519 mg; potassium citrate, 2.549 mmol and 781.183 mg; calcium glycerophosphate, 2.377 mmol and 499.478 mg; magnesium gluconate, 0.482 mmol and 199.791 mg; manganese sulfate, 0.006 mmol and 0.932 mg; ferrous sulfate, 0.059 mmol and 8.991 mg; copper gluconate, 0.002 mmol and 0.999 mg; sodium selenite, 0.00029 mmol and 0.050 mg; sodium molybdate, and 0.00018 mmol and 0.038 mg; chromium chloride, 0.00011 mmol and 0.017 mg; sodium phosphate dibasic, 3.518 mmol and 499.478 mg; and potassium iodide, 0.00045 mmol and 0.075 mg.

Again, the total sums of the number of moles and the equivalent weights of each of the fatty acids, vitamins, and mineral nutrients in the another mixtures, above, may be varied by multiplying each of the number of moles and the equivalent weights by a proportional factor relative to the total number of 650 mmol for the mixture of amino acids. For example, to obtain the number of moles and equivalent weights of the another mixture of fatty acids, vitamins, and mineral nutrients to be added to either an aqueous mixture of amino acids having a calculated osmolarity of 120 mmol/liter or a powdered mixture of amino acids having a total sum of a number of moles equaling 120 mmol, each of the number of moles and equivalent weights of the another mixture of fatty acids, vitamins, and mineral nutrients, above, may be multiplied by a proportional factor of about 0.185. Similarly, to obtain the number of moles and equivalent weights of the another mixture of fatty acids, vitamins, and mineral nutrients to be added to either an aqueous mixture of amino acids having a calculated osmolarity of 1000 mmol/liter or a powdered mixture of amino acids having a total sum of a number of moles equaling 1000 mmol, each of the number of moles and equivalent weights of the another mixture of fatty acids, vitamins, and mineral nutrients, above, may be multiplied by a proportional factor of about 5.42.

D. Other Constituents

A single composition, to be topically applied at a wound site to inhibit infection and provide one or more nutrients, may comprise a mixture of: amino acids; and yet another mixture of any of amino acid derivatives, preservatives, an emulsifier, and a hydrogel agent where a sum of the number of moles of the mixture of amino acids is proportional to sums of the number of moles and equivalent weights of each of the constituents of the yet another mixture of amino acid derivatives, preservatives, and emulsifiers.

When the sum of the number of moles in any of the mixtures of aqueous amino acids or powdered amino acids, described above, is 650 mmol, the yet another mixture of any of amino acid derivatives, preservatives, an emulsifier, and a hydrogel in the single composition, directly above, may comprise the following proportional number of moles and equivalent weights, plus or minus 5 percent: L-taurine, 0.962 mmol and 120.407 mg; L-carnitine, 0.840 mmol and 135.458 mg; ascorbyl palmitate, 0.013 mmol and 5.328 mg; and butylated hydroxytoluene (BHT)/butylated hydroxyanisole (BHA), 0.007 mmol and 1.332 mg. The yet another mixture may further comprise the following proportional number of moles and equivalent weights, plus or minus 5 percent: potassium sorbate (a preservative), 2.216 mmol and 332.985 mg; Polysorbate 80 (an emulsifier), 0.041 mmol and 53.278 mg. The yet another mixture may yet further comprise a hydrogel agent, e.g., methyl cellulose, sufficient in quantity to form a hydrogel including any of the aqueous mixtures of amino acids, described above.

Again, the total sums of the number of moles and the equivalent weights of any of the amino acid derivatives, the preservatives, the amino acid derivatives, the emulsifier, and the hydrogel agent in the yet another mixtures, above, may be varied by multiplying each of the number of moles and the equivalent weights by a proportional factor relative to the total number of 650 mmol for the mixture of amino acids. For example, to obtain the number of moles and equivalent weights of the yet another mixture of any of the amino acid derivatives, the preservatives, the amino acid derivatives, the emulsifier, and the hydrogel agent, to be added to either an aqueous mixture of amino acids having a calculated osmolarity of 120 mmol/liter or a powdered mixture of amino acids having a total sum of a number of moles equaling 120 mmol, each of the number of moles and equivalent weights of the yet another mixture of any of the amino acid derivatives, the preservatives, the amino acid derivatives, the emulsifier, and the hydrogel agent, above, may be multiplied by a proportional factor of about 0.185. Similarly, to obtain the number of moles and equivalent weights of the yet another mixture of any of the amino acid derivatives, the preservatives, the amino acid derivatives, the emulsifier, and the hydrogel agent, to be added to either an aqueous mixture of amino acids having a calculated osmolarity of 1000 mmol/liter or a powdered mixture of amino acids having a total sum of a number of moles equaling 1000 mmol, each of the number of moles and equivalent weights of the yet another mixture of any of the amino acid derivatives, the preservatives, the amino acid derivatives, the emulsifier, and the hydrogel agent, above, may be multiplied by a proportional factor of about 5.42.

EXAMPLES

The following examples are included to demonstrate preferred embodiments of the disclosure. However, those of skill in the art should, in light of the present disclosure, appreciate that many changes can be made in the specific embodiments which are disclosed and still obtain a like or similar result without departing from the spirit and scope of the disclosure.

Example 1

A single composition, to be topically applied at a wound site to inhibit bacterial infection and provide one or more nutrients, that may comprise a mixture of amino acids, including each of the indispensable amino acids and each of the following conditionally indispensable and dispensable amino acids. Table 1 specifies the following proportional number of moles and equivalent weights, plus or minus 5 percent, for a mixture of amino acids having a total number of moles equal to 650 mmol in the single composition.

TABLE 1

| | |
|---|---|
| histidine•HCl•H$_2$O | 9.743 mmol and 2.042 g |
| isoleucine | 54.594 mmol and 7.157 g |
| leucine | 109.264 mmol and 14.332 g |
| lysine acetate | 21.402 mmol and 4.414 g |
| methionine | 21.229 mmol and 3.168 g |
| phenylalanine | 27.034 mmol and 4.466 g |
| threonine | 29.062 mmol and 3.462 g |
| tryptophan | 5.424 mmol and 1.108 g |
| valine | 61.095 mmol and 7.157 g |
| alanine | 50.321 mmol and 4.483 g |
| arginine acetate | 28.227 mmol and 6.612 g |
| aspartic acid | 54.582 mmol and 6.067 g |
| glutamine | 76.100 mmol and 11.121 g |
| glycine | 46.232 mmol and 3.471 g |
| proline | 36.684 mmol and 4.223 g |
| serine | 24.130 mmol and 2.536 g |
| tyrosine | 4.012 mmol and 0.727 g |

Example 2

A single composition, to be topically applied at a wound site to inhibit bacterial infection and provide one or more nutrients, that may comprise a mixture of: amino acids, including each of the indispensable amino acids and each of the following conditionally indispensable and dispensable amino acids; and a carbohydrate. Table 2 specifies the following proportional number of moles and equivalent weights, plus or minus 5 percent, for a mixture of amino acids having a total number of moles equal to 650 mmol and a carbohydrate in the single composition.

TABLE 2

| | |
|---|---|
| histidine•HCl•H$_2$O | 9.743 mmol and 2.042 g |
| isoleucine | 54.594 mmol and 7.157 g |
| leucine | 109.264 mmol and 14.332 g |
| lysine acetate | 21.402 mmol and 4.414 g |
| methionine | 21.229 mmol and 3.168 g |
| phenylalanine | 27.034 mmol and 4.466 g |
| threonine | 29.062 mmol and 3.462 g |
| tryptophan | 5.424 mmol and 1.108 g |
| valine | 61.095 mmol and 7.157 g |
| alanine | 50.321 mmol and 4.483 g |
| arginine acetate | 28.227 mmol and 6.612 g |
| aspartic acid | 54.582 mmol and 6.067 g |
| glutamine | 76.100 mmol and 11.121 g |
| glycine | 46.232 mmol and 3.471 g |
| proline | 36.684 mmol and 4.223 g |
| serine | 24.130 mmol and 2.536 g |
| tyrosine | 4.012 mmol and 0.727 g |
| maltodextrin | 120.33 mmol and 205.45 g |

Example 3

A single composition, to be topically applied at a wound site to inhibit bacterial infection and provide one or more nutrients, that may comprise a mixture of: amino acids, including each of the indispensable amino acids and each of the following conditionally indispensable and dispensable amino acids; a carbohydrate; another mixture of fatty acids, vitamins, and mineral nutrients; and yet another mixture of amino acid derivatives and preservatives. Table 3 specifies the following proportional number of moles and equivalent weights, plus or minus 5 percent, for a mixture of amino acids having a total number of moles equal to 650 mmol in the single composition.

TABLE 3

| | |
|---|---|
| histidine•HCl•H$_2$O | 9.743 mmol and 2.042 g |
| isoleucine | 54.594 mmol and 7.157 g |
| leucine | 109.264 mmol and 14.332 g |
| lysine acetate | 21.402 mmol and 4.414 g |
| methionine | 21.229 mmol and 3.168 g |
| phenylalanine | 27.034 mmol and 4.466 g |
| threonine | 29.062 mmol and 3.462 g |
| tryptophan | 5.424 mmol and 1.108 g |
| valine | 61.095 mmol and 7.157 g |
| alanine | 50.321 mmol and 4.483 g |
| arginine acetate | 28.227 mmol and 6.612 g |
| aspartic acid | 54.582 mmol and 6.067 g |
| glutamine | 76.100 mmol and 11.121 g |
| glycine | 46.232 mmol and 3.471 g |
| proline | 36.684 mmol and 4.223 g |
| serine | 24.130 mmol and 2.536 g |
| tyrosine | 4.012 mmol and 0.727 g |
| maltodextrin | 120.33 mmol and 205.45 g |
| alpha-linolenic acid | 47.836 mmol and 13.319 g |
| vitamin A palmitate | 2.617 µmol and 1.374 mg |
| cholecalciferol (D3) | 0.013 µmol and 0.0050 mg |
| alpha tocopherol (E) | 23.35 µmol and 10.057 mg |
| pantothenic acid (B5) | 45.567 µmol and 9.990 mg |
| zinc sulfate | 61.866 µmol and 9.990 mg |
| L-taurine | 0.962 mmol and 120.407 mg |
| L-carnitine | 0.840 mmol and 135.458 mg |
| ascorbyl palmitate | 0.013 mmol and 5.328 mg |
| BHT/BHA | 0.007 mmol and 1.332 mg |

Example 4

A single composition, to be topically applied at a wound site to inhibit bacterial infection and provide one or more nutrients, that may comprise a mixture of: amino acids, including each of the indispensable amino acids and each of the following conditionally indispensable and dispensable amino acids; a carbohydrate; another mixture of fatty acids, vitamins, and mineral nutrients; and yet another mixture of amino acid derivatives and preservatives. Table 4 specifies the following proportional number of moles and equivalent weights, plus or minus 5 percent, for a mixture of amino acids having a total number of moles equal to 650 mmol in the single composition.

TABLE 4

| | |
|---|---|
| histidine•HCl•H$_2$O | 9.743 mmol and 2.042 g |
| isoleucine | 54.594 mmol and 7.157 g |
| leucine | 109.264 mmol and 14.332 g |
| lysine acetate | 21.402 mmol and 4.414 g |
| methionine | 21.229 mmol and 3.168 g |
| phenylalanine | 27.034 mmol and 4.466 g |
| threonine | 29.062 mmol and 3.462 g |
| tryptophan | 5.424 mmol and 1.108 g |
| valine | 61.095 mmol and 7.157 g |
| alanine | 50.321 mmol and 4.483 g |
| arginine acetate | 28.227 mmol and 6.612 g |
| aspartic acid | 54.582 mmol and 6.067 g |
| glutamine | 76.100 mmol and 11.121 g |
| glycine | 46.232 mmol and 3.471 g |
| proline | 36.684 mmol and 4.223 g |
| serine | 24.130 mmol and 2.536 g |
| tyrosine | 4.012 mmol and 0.727 g |
| maltodextrin | 120.33 mmol and 205.45 g |
| alpha-linolenic acid | 47.836 mmol and 13.319 g |
| vitamin A palmitate | 2.617 µmol and 1.374 mg |
| cholecalciferol (D3) | 0.013 µmol and 0.0050 mg |
| alpha tocopherol (E) | 23.35 µmol and 10.057 mg |
| pantothenic acid (B5) | 45.567 µmol and 9.990 mg |

TABLE 4-continued

| | |
|---|---|
| vitamin C (ascorbic acid) | 340.321 µmol and 59.937 mg |
| folic acid | 0.905 µmol and 0.400 mg |
| thiamine hydrochloride | 5.647 µmol and 1.498 mg |
| riboflavin | 4.512 µmol and 1.698 mg |
| niacinamide | 163.602 µmol and 19.979 mg |
| vitamin B6 | 13.473 µmol and 3.30 mg |
| cyanocobalamin (B12) | 0.004 µmol and 0.0060 mg |
| biotin | 1.227 µmol and 0.300 mg |
| phytonadione (K1) | 0.089 µmol and 0.040 mg |
| choline bitartrate | 706.433 µmol and 75.590 mg |
| potassium chloride | 8.040 mmol and 599.373 mg |
| sodium citrate | 2.146 mmol and 459.519 mg |
| potassium citrate | 2.549 mmol and 781.183 mg |
| calcium glycerophosphate | 2.377 mmol and 499.478 mg |
| magnesium gluconate | 0.482 mmol and 199.791 mg |
| manganese sulfate | 0.006 mmol and 0.932 mg |
| ferrous sulfate | 0.059 mmol and 8.991 mg |
| copper gluconate | 0.002 mmol and 0.999 mg |
| sodium selenite | 0.00029 mmol and 0.050 mg |
| sodium molybdate | 0.00018 mmol and 0.038 mg |
| chromium chloride | 0.00011 mmol and 0.017 mg |
| sodium phosphate dibasic | 3.518 mmol and 499.478 mg |
| potassium iodide | 0.00045 mmol and 0.075 mg |
| zinc sulfate | 61.866 µmol and 9.990 mg |
| L-taurine | 0.962 mmol and 120.407 mg |
| L-carnitine | 0.840 mmol and 135.458 mg |
| ascorbyl palmitate | 0.013 mmol and 5.328 mg |
| potassium sorbate | 2.216 mmol and 332.985 mg |
| Polysorbate 80 | 0.041 mmol and 53.278 mg |
| BHT/BHA | 0.007 mmol and 1.332 mg |

All of the methods and compositions disclosed and claimed herein can be made and executed without undue experimentation in light of the present disclosure. While the methods and compositions of this disclosure are described in terms of preferred embodiments, it will be apparent to those of skill in the art that variations may be applied to the methods and compositions herein without departing from the concept, spirit, and scope of the disclosure. More specifically, it will be apparent that certain agents which are chemically and physiologically related may be substituted for the agents described herein while the same or similar results would be achieved. All such similar substitutes and modifications, apparent to those skilled in the art are deemed to be within the spirit, scope and concept of the disclosure as defined by the appended claims.

What is claimed is:

1. A method that inhibits infection during wound healing comprising topically applying a single composition that contacts a wound to initiate wound healing, said single composition consisting of:

a mixture of amino acids with the following proportional number of moles, plus or minus 5 percent: histidine monohydrochloride monohydrate, 9.743 mmol; isoleucine, 54.594 mmol; leucine, 109.264 mmol; lysine acetate, 21.402 mmol; methionine, 21.229 mmol; phenylalanine, 27.034 mmol; threonine, 29.062 mmol; tryptophan, 5.424 mmol; valine, 61.095 mmol; alanine, 50.321 mmol; arginine acetate, 28.227 mmol; aspartic acid, 54.582 mmol; glutamine, 76.100 mmol; glycine, 46.232 mmol; proline, 36.684; serine, 24.130 mmol; and tyrosine, 4.012 mmol, a first sum of said proportional number of moles of said mixture of amino acids equaling 650.135 mmol, plus or minus 5 percent, each of said proportional number of moles of said first sum being multiplied by a proportional factor of about 1.538 to provide a second sum of said proportional number of moles of said mixture of amino acids of about 1000 mmol, said about 1000 mmol of said second sum of said proportional number of moles of said mixture of amino acids being mixed in one liter of water; and a carbohydrate consisting of one member selected from the group of: D-glucose, sucrose, and a maltodextrin, a number of moles of said carbohydrate being determined by a proportion of about 1.00 moles of said carbohydrate to about 5.40 moles of said second sum of said proportional number of moles of said mixture of amino acids of about 1000 mmol, said number of moles of said carbohydrate being added to said second sum of said proportional number of moles of said mixture of amino acids in said one liter of water, to inhibit infection.

2. A method that inhibits infection during wound healing comprising topically applying a single composition that contacts a wound to initiate wound healing, said single composition consisting of:

an aqueous mixture of amino acids with the following proportional number of moles, plus or minus 5 percent: histidine monohydrochloride monohydrate, 9.743 mmol; isoleucine, 54.594 mmol; leucine, 109.264 mmol; lysine acetate, 21.402 mmol; methionine, 21.229 mmol; phenylalanine, 27.034 mmol; threonine, 29.062 mmol; tryptophan, 5.424 mmol; valine, 61.095 mmol; alanine, 50.321 mmol; arginine acetate, 28.227 mmol; aspartic acid, 54.582 mmol; glutamine, 76.100 mmol; glycine, 46.232 mmol; proline, 36.684; serine, 24.130 mmol; and tyrosine, 4.012 mmol, a first sum of said proportional number of moles of said mixture of amino acids being 650 mmol, said 650 mmol of said first sum of said proportional number of moles of said aqueous mixture of amino acids being mixed in one liter of water; and a mixture of fatty acids, vitamins, and a mineral nutrient with the following proportional number of moles, plus or minus 5 percent, consisting oft one of: alpha linolenic acid, 47.836 mmol and linolenic acid, 47.494 mmol; and a combination of 23.918 mmol of alpha linoleic acid and 23.747 mmol of linoleic acid; vitamin A palmitate, 2.617 µmol; vitamin D3 (cholecalciferol), 0.013 µmol; vitamin E (alpha tocopherol), 23.35 µmol; pantothenic acid (vitamin B5), 45.567 µmol; and zinc sulfate, 61.866 µmol, a sum of said number of moles of said mixture of fatty acids, vitamins, and a mineral nutrient being added to said first sum of said proportional number of moles of said mixture of amino acids in said one liter of water, to inhibit infection.

3. A method that inhibits infection during wound healing comprising topically applying a single composition that contacts a wound to initiate wound healing, said single composition consisting of:

an aqueous mixture of amino acids with the following proportional number of moles, plus or minus 5 percent: histidine monohydrochloride monohydrate, 9.743 mmol; isoleucine, 54.594 mmol; leucine, 109.264 mmol; lysine acetate, 21.402 mmol; methionine, 21.229 mmol; phenylalanine, 27.034 mmol; threonine, 29.062 mmol; tryptophan, 5.424 mmol; valine, 61.095 mmol; alanine, 50.321 mmol; arginine acetate, 28.227 mmol; aspartic acid, 54.582 mmol; glutamine, 76.100 mmol; glycine, 46.232 mmol; proline, 36.684; serine, 24.130 mmol; and tyrosine, 4.012 mmol, a first sum of said proportional number of moles of said mixture of amino acids being 650 mmol; and a mixture of any of amino acid derivatives, preservatives, and an emulsifier with the following proportional number of moles, plus or minus 5 percent, consisting of: L-taurine, 0.962 mmol; L-carnitine, 0.840 mmol; ascorbyl palmitate, 0.013 mmol; potassium sorbate, 2.216 mmol; Polysorbate 80, 0.041 mmol; and of methyl cellulose sufficient to form a hydrogel in the aqueous mixture of amino acids, a second sum of said proportional number of moles of said mixture of amino acid derivatives, preservatives, and an emulsifier, and of the methyl cellulose sufficient to form the hydrogel being added to said first sum of said proportional number of moles of said mixture of amino acids in said single composition, to inhibit infection.

* * * * *